(12) United States Patent
McClellan et al.

(10) Patent No.: US 8,491,923 B2
(45) Date of Patent: Jul. 23, 2013

(54) METHOD FOR CONTROLLING FUNGI AND MITES IN TEXTILE SUBSTRATES

(75) Inventors: William D. McClellan, Wilmington, DE (US); Eric C. Tedford, Roseville, CA (US); Jeremy R. Godwin, Maisprach (CH)

(73) Assignee: LANXESS Deutschland GmbH, Leverkusen (DE)

( * ) Notice: Subject to any disclaimer, the term of this patent is extended or adjusted under 35 U.S.C. 154(b) by 1582 days.

(21) Appl. No.: 10/576,376

(22) PCT Filed: Nov. 22, 2004

(86) PCT No.: PCT/US2004/039373
§ 371 (c)(1),
(2), (4) Date: Mar. 7, 2007

(87) PCT Pub. No.: WO2005/053400
PCT Pub. Date: Jun. 16, 2005

(65) Prior Publication Data
US 2007/0225298 A1    Sep. 27, 2007

Related U.S. Application Data

(60) Provisional application No. 60/525,605, filed on Nov. 26, 2003.

(51) Int. Cl.
*A01N 25/34* (2006.01)
(52) U.S. Cl.
USPC ........... 424/409; 424/403; 424/404; 424/405; 514/269; 514/344; 514/531
(58) Field of Classification Search
None
See application file for complete search history.

(56) References Cited

U.S. PATENT DOCUMENTS

| | | |
|---|---|---|
| 246,335 A | 8/1881 | Page |
| 3,769,060 A | 10/1973 | Ida et al. |
| 3,837,988 A * | 9/1974 | Hennen et al. ................ 428/92 |
| 4,666,940 A | 5/1987 | Bischoff et al. |
| 4,705,800 A | 11/1987 | Nyfeler et al. |
| 5,395,837 A | 3/1995 | Clough et al. |
| 5,527,582 A | 6/1996 | Callebert |
| 5,843,981 A | 12/1998 | Miller |
| 5,916,580 A | 6/1999 | Shober et al. |
| 6,117,440 A * | 9/2000 | Suh et al. ..................... 424/407 |
| 6,440,438 B2 | 8/2002 | Platts |
| 6,463,963 B1 | 10/2002 | Moody et al. |
| 6,624,179 B1 | 9/2003 | Koyanagi et al. |
| 2002/0176854 A1 | 11/2002 | Payton |

FOREIGN PATENT DOCUMENTS

| | | |
|---|---|---|
| EP | 1228689 A1 | 7/2002 |
| EP | 0 090 552 A2 | 4/2011 |
| FR | 2 763 928 A1 | 6/1997 |
| WO | WO-92-08397 A1 | 5/1992 |
| WO | WO-98-47358 A1 | 10/1998 |
| WO | WO-99-21421 A1 | 5/1999 |
| WO | WO-99-53763 A1 | 10/1999 |
| WO | WO-00-03593 A1 | 1/2000 |
| WO | WO-01-41564 A2 | 6/2001 |
| WO | WO-01-41564 A3 | 6/2001 |
| WO | WO 02/35930 * | 5/2002 |

OTHER PUBLICATIONS

European Search Report from co-pending Application EP04811990 dated Mar. 12, 2012, 3 pages.

* cited by examiner

*Primary Examiner* — Neil Levy
(74) *Attorney, Agent, or Firm* — Nicanor A. Kohneke

(57) ABSTRACT

The present invention, therefore, relates to a method for prophylaxis, control or reduction of fungi in a textile substrate, which comprises applying to a textile substrate that is susceptible to fungal infestation an amount effective for the prophylaxis, control or reduction of fungi of at least one fungicidal compound. The invention further provides a method for the prophylaxis, control or reduction of both fungi and dust mites in a textile substrate, which comprises co-application to a textile substrate that is susceptible to fungal and dust mite infestation of a prophylactic or acaricidally effective amount of a suitable acaricide and a prophylactic or fungicidally effective amount of at least one fungicidal compound.

6 Claims, No Drawings ized over approximately 25 days through
METHOD FOR CONTROLLING FUNGI AND MITES IN TEXTILE SUBSTRATES This application is a 371 of International Application No. PCT/US2004/039373 filed Nov. 22, 2004, which claims priority to U.S. 60/525,605 filed Nov. 26, 2003, the contents of which are incorporated herein by reference.

FIELD OF THE INVENTION

This invention relates to a method for controlling the growth or proliferation of fungi in textile substrates. The invention further relates to a method for controlling the growth or proliferation of both fungi and dust mites in textile substrates.

BACKGROUND OF THE INVENTION

Increasing attention is being focused on the importance of good indoor air quality and its affect on health. The U.S. Environmental Protection Agency (EPA) has named indoor air pollution as one of the most urgent national problems. While many factors can contribute to poor indoor air quality, much attention has recently been given to the detrimental affects of fungi such as molds and yeasts. For example, a Mayo Clinic study published in 1999, identified fungi as a leading cause of many respiratory problems, and a contributor to nearly 100% of chronic sinus infections. In addition to allergies, the Mayo study suggests that many people also develop a different kind of immune system response to fungi.

Molds and fungi produce at least two types of potential allergens: (a) Mycelia produced enzymes, and (b) Fungal spores. Regarding the former, molds feed off decomposing plant and animal matter and grow by producing filament-like extensions called "mycelia." These filaments secrete enzymes that can digest carbohydrates and proteins. These enzymes are very small and can go airborne in some form. In heavy concentrations, mold enzymes may become allergens. As to the latter, molds reproduce by giving off huge numbers of mold spores into the air, similar to plants releasing pollen. When airborne mold spores settle on organic matter, new mold growth starts. As protein is a significant component of mold spores, they may trigger an allergic reaction when inhaled. Such spores can be as small a 2 microns (*Aspergillus fumigatus*) and as large as 140 microns (*Alternaria*).

A particularly good environment for the growth of mold spores is found in carpet, carpet tile and upholstery. For example, fungi are deposited on the carpet through the everyday traffic of people and animals, food and beverages spilled on the carpet, and animal and infant waste. Further, airborne fungi and spores carried in from outside or carried through the heating or cooling system can accumulate on carpet and upholstery. Soil and moisture in carpet can provide nutrients for the growth of the fungi. Moreover, certain fungal spores are capable of remaining viable in a dormant state on carpet for long periods of time until they are provided adequate sustenance.

In addition to mold spores, the common house dust mite is an important cause of asthma, rhinitis, atopic dermatitis eczema in allergic individuals. For example, the mite *Dermatophygoides pteronyssinus* has been identified as a major source of house dust allergen. This mite and the related mites *D. farinae, D. microceras* and *Euroglyphus maynei* are the predominant house dust mites in temperate climates in North America, Australia and other areas.

Adult mites are approximately 300 microns (3/10 mm) in size, having developed over approximately 25 days through egg, larval and nymph stages. Adults live for 2 to 3½ months, during which time each female can produce about 20-40 eggs. Dust mites are photophobic, living deep in pillows, mattresses, carpets, upholstered furniture and other soft materials. Literally millions of mites can inhibit a single bed or rug.

A major dust mite allergen is present in mite faecal particles. Each mite produces about 20 faecal particles per day, and more than 100,000 of them may be present in a gram of dust. These particles vary from about 10 to 40 microns in size, comparable to the size of mold spores, and become airborne during domestic activity such as making beds and vacuuming carpets.

Although carpets and upholstered furniture are major sites of mold and dust mite growth, many allergic individuals are unable or unwilling to remove these from their home. Ordinary vacuuming does not remove mold and dust mites or significantly decrease mold and dust mite allergen levels, and in fact, vacuuming of carpets with the usual household appliances actually increases the amount of airborne dust. However, the use of special filters and/or the employment of central vacuuming systems have been helpful. Nevertheless, vacuuming alone seldom removes all of the mites or molds.

Thus, it would be desirable to have an effective method of controlling the growth of fungi such as molds in carpets and other textile substrates. It would also be desirable to have a method for controlling both fungal growth and house dust mites in carpets and other textile substrates.

SUMMARY OF THE INVENTION

The present invention is focused on the use of fungicidal compounds to provide desirable antifungal efficacy in textile substrates and products. Surprisingly it was found that selected fungicidal compounds can be applied to various textile substrates made of man made as well as natural fibers to provide antifungal activities and, when combined with an acaricide, anti-dust mite properties in the living environments of human beings and animals. It was found that the treatment of such textile substrates/products with selected fungicidal compounds and/or formulations that contain such compounds can be carried out in various processes such as spraying, misting, atomising, broadcasting, brushing, raking and foaming application processes. Such applications are optionally conducted in combination with a vacuuming and/or hot water extraction step.

The present invention, therefore, relates to a method for prophylaxis, control or reduction of fungi in a textile substrate, which comprises applying to a textile substrate that is susceptible to fungal infestation an amount effective for the prophylaxis, control or reduction of fungi of at least one fungicidal compound. The invention further provides a method for the prophylaxis, control or reduction of both fungi and dust mites in a textile substrate, which comprises coapplication to a textile substrate that is susceptible to fungal and dust mite infestation of a prophylactic or acaricidally effective amount of a suitable acaricide and a prophylactic or fungicidally effective amount of at least one fungicidal compound.

More specifically, the present invention provides a method for prophylaxis, control or reduction of fungi, especially allergenic, toxinogenic and immunogenic fungi, that is particularly suitable for the management of such fungi in textile substrates such as carpets. The method of the present invention comprises contacting the textile substrate to be treated with a prophylactic or fungicidally (and, optionally, acaricidally) effective amount of pesticidal composition comprising a fungicidally active ingredient and, optionally, an acaricide along with a textile acceptable carrier or diluent. The invention also relates to such pesticidal compositions that are suitable for application to textile substrates such as carpets.

The invention further relates to a process for prophylaxis, control or reduction of fungi and dust mite populations in textile substrates and the allergens, toxinogens and/or immunogens resulting therefrom by using a pesticidal composition according to the invention. It also relates to the said textile materials treated with the said composition.

The concentration of allergens, toxinogens and/or immunogens produced by the fungi and dust mites can be reduced or controlled in accordance with the method of this invention by applying the pesticidal composition according to the invention onto or, preferably, below the surface of textile substrates such as carpets which contain or are susceptible to contain mites and molds. The mites and molds are thus killed or controlled and the production of additional allergens, toxinogens and/or immunogens is thereby reduced. Advantageously, the method of the invention optionally includes a step for removal of fungi including molds, mycelium and spores thereof, live or dead mites and faecal matter thereof by employing a vacuuming apparatus and/or by hot water extraction preferably under conditions wherein the removed material is substantially not vented into the local atmosphere.

DETAILED DESCRIPTION OF THE INVENTION

In one embodiment, the method of this invention comprises the steps of (1) providing a textile treatment composition comprising (i) a fungicidal compound and, optionally, (ii) an acaricide, (2) providing a textile substrate that is susceptible to fungal infestation (and, optionally, dust mite infestation); and (3) contacting the textile substrate with a prophylactic or fungicidally (and, optionally, acaricidally) effective amount of the treatment composition. In one embodiment, the method further comprises (4) allowing a suitable period of time for the textile substrate to dry, and (5) removing fungi including molds, mycelium and spores thereof, live or dead mites and faecal matter thereof by employing a vacuuming apparatus and/or by hot water extraction preferably under conditions wherein the removed material is substantially not vented into the local atmosphere. In another embodiment, the vacuuming and/or hot water extraction step is conducted prior to step (1). This sequence is particularly suited to a method where prophylactic amounts of the composition are employed.

As used herein, the term "fungicidal compound" shall mean a material that kills or materially inhibits the growth, proliferation, division, reproduction, or spread of fungi including, but not limited to, allergenic, toxinogenic and immunogenic fungi. As used herein, the term "prophylactic or fungicidally effective amount" or "amount effective to control or reduce fungi" in relation to the fungicidal compound is that amount that will kill or materially inhibit the growth, proliferation, division, reproduction, or spread of a significant number of fungi such as molds and, in particular, allergenic, toxinogenic or immunogenic varieties thereof in a target textile substrate.

Suitable classes of fungicidal compounds include strobilurin fungicides, pyrrole fungicides, anilide fungicides, conazole fungicides such as the imidazoles and triazoles, thiazole fungicides and pyrimidine fungicides as well as mixtures thereof.

Different fungicide biochemical modes of actions may be selected for resistance management. In one embodiment, mixtures of fungicides having different biochemical modes of action are applied to the textile substrate. In one embodiment, subsequent applications of fungicides comprise a fungicide having a different biochemical mode of action from the fungicide used in the previous application. Timing of subsequent applications, if necessary, can vary depending upon the efficacy of the fungicide selected and the levels of fungi present in the textile substrate.

Suitable strobilurin fungicides useful in the method of the invention include, for example, azoxystrobin, dimoxystrobin, fluoxastrobin, picoxystrobin and pyraclostrobin.

In one embodiment, the strobilurin fungicide used in the method of the invention is azoxystrobin. Azoxystrobin is represented by the formula (I)

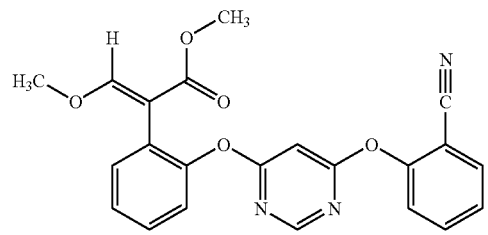 [SMILES: CO/C=C(/C(=O)OC)c1ccccc1Oc1cc(Oc2ccccc2C#N)ncn1]

This compound, its synthesis as well as its fungicidal properties are described in U.S. Pat. No. 5,395,837, which is incorporated herein by reference.

Suitable pyrrole fungicides useful in the method of the invention include, for example, fludioxonil.

In one embodiment, the pyrrole fungicide used in the method of the invention is fludioxonil. Fludioxonil, is represented by the formula (II)

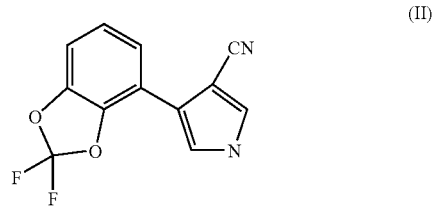 [SMILES: N#Cc1c[nH]cc1-c1cccc2c1OC(F)(F)O2]

This compound, its synthesis as well as its fungicidal properties are described in U.S. Pat. No. 4,705,800, which is incorporated herein by reference.

Suitable anilide fungicides useful in the method of the invention include boscalid.

Suitable conazole fungicides useful in the method of the invention include difenoconazole, propiconazole, tebuconazole, epoxiconazole, flusilazole and metconazole.

Suitable thiazole fungicides useful in the method of the invention include thiabendazole.

Suitable pyrimidine fungicides useful in the method of the invention include cyprodinil and pyrimethanil.

Preferred fungicides useful in the method of the invention include the strobilurin and pyrrole fungicides.

In one embodiment, the method according to the invention is used in the management, prophylaxis or control of fungi such as molds and, in particular, allergenic, toxinogenic or immunogenic varieties thereof, in textile materials such as, for example, indoor carpets. The following genera of fungi may be mentioned by way of example but without imposing any limitation: for example, *Alternaria* spp., such as *A. alternate, A. tenuis; Cladosporium* spp., such as *C. cladosporioides, C. herbarum; Penicillium* spp., such as *P. chrysogenum, P. brevicaule, P. brevicompactum P. glaucum* and *P. pinophi-*

*lum; Aspergillus* spp., such as *A. versicolor, A. fumigatus, A. flavus, A. eustis, A. niger,* and *A. terreus.; Memnoniella* spp.; *Stachybotris* spp.; *Aureobasidium* spp., such as, *A. pullulans; Chaetomium* spp., such as *C. globosum, C. funicola; Acremonium* spp., such as *A. strictum; Ulocladium* spp., such as *U. chartarum; Pithomyces* spp.; *Chrysonfila* spp.; *Mucor* spp.; *Coniophora* spp., such as *C. puteana; Gliocladium* spp., such as *G. virens; Lentinus* spp., such as *L. tigrinus; Paecilomyces* spp., such as *P. varioti; Polyporus* spp., such as *P. versicolor; Sclerophoma* spp., such as *S. pityophila; Streptoverticillium* spp., such as *S. reticulum.*

As used herein, the term "acaricide" shall mean a material that kills or materially inhibits the growth, proliferation, reproduction, or spread of acarids including, but not limited to, dust mites such as *Dermatophigoides pteronyssinus, D. farinae, D. microceras* and *Euroglyphus maynei.* An "prophylactic or acaricidally effective amount" of an acaricide is that amount that will kill or materially inhibit the growth, proliferation, reproduction or spread of a significant number of acarids in the target textile substrate.

Suitable acaricides that can be used in combination with the fungicides in accordance with the method of the invention include, for example, compounds known under the common names as benzyl benzoate, disodium octaborate tetrahydrate, diafenthiuron, primiphos-methyl, pyridaben, insect growth regulators such as methoprene and hydroprene, pyrethroid compounds such as cyhalothrin, gamma-cyhalothrin, lambda-cyhalothrin, resmethrin, phenothrin, permethrin, allethrins, tetramethrin, furamethrin, fenvalerate, terallethrin, empenthrin, pyrethrin and natural pyrethrins; 1-ethynyl-2-methyl-2-pentenyl-2,2-dimethyl-3-3-(2,2-dichlorovinyl)-cyclopropane-1-carboxylate, 1-ethynyl-2-methyl-2-pentenyl-2,2,3,3-tetramethylcyclopropane-1-carboxylate, α-cyano-3-phenoxybenzyl-2,2-dimethyl-3-(2,2,3-tribromethyl)-cyclopropane-1-carboxylate; spinosad, p-anisaldehyde, abamectin, emamectin and esters thereof such as emamectin benzoate, ivermectin, and milbemycins. Permethrin is a preferred acaracide.

The terms "active component(s)", "active compound(s)" or "active ingredient(s)" (a.i.) are used to herein refer to the fungicide compound, compound mixtures or mixtures with an acaricide such as permethrin, as the case may be, that are used directly or in formulation with other materials for application to target textile substrates, materials or surfaces in accordance with the method of the invention.

The activity and the spectrum of action of the active components according to the invention or of the agents, concentrates or, generally, formulations prepared therewith, is increased if, if appropriate, other antimicrobially active substances, fungicides, insecticides or other active compounds are added to widen the spectrum of the active compound or to achieve specific effects such as, for example, a denaturing agent which breaks down dead fungi including molds, mycelium and spores thereof, mites and faecal matter thereof or disinfectants which disinfect by destroying, neutralizing or inhibiting the growth of microorganisms such as bacteria, viruses and protozoa. Suitable denaturants include tannic acid or enzymes.

In one embodiment, the active components are processed in known manner to give compositions formulated as, for example, dispersible concentrates, emulsifiable concentrates, suspension concentrates, microemulsifiable concentrates, soluble liquids, microemulsions, suspoemulsions, directly sprayable or dilutable solutions, dilute emulsions, aerosols, powders, dusts, granules or encapsulations in polymeric substances which comprise at least one of the active components.

The compositions mentioned are prepared in a manner known per se, for example by mixing the active compounds with a solvent or with diluents, emulsifiers, dispersants, surfactants and/or binders or fixatives, if appropriate desiccants and UV stabilisers and if appropriate colours and pigments and other processing auxiliaries.

Suitable solvents or diluents are organochemical solvents such as aromatic hydrocarbons, in particular the fractions $C_8$ to $C_{12}$, such as xylene mixtures or substituted naphthalenes, phthalic esters such as dibutly or dioctyl phthalate, aliphatic hydrocarbons such as cyclohexane or paraffins, alcohols and glycols as well as their ethers and esters, such as ethylene glycol monomethyl ether, ethylene, propylene or butylene carbonate, ketones such as cyclohexanone, strongly polar solvents such as N-methyl-2-pyrrolidone, dimethyl sulfoxide or dimethylformamide, and, if appropriate, epoxidized vegetable oils or soybean oil; or water or solvent mixtures.

Preferred suitable solvents or diluents include water and tetrahydrofurfuryl alcohol, if appropriate as a mixture with one or more of the solvents or diluents, emulsifiers and dispersants which are customarily used.

Suitable surface-active compounds are non-ionic, cationic and/or anionic surfactants having good emulsifying, dispersing and wetting properties, depending on the nature of the active components to be formulated. Surfactants will also be understood as meaning mixtures of surfactants.

The surfactants customarily employed in formulation technology are described, inter alia, in the following publications: "McCutcheon's Detergents and Emulsifiers Annual", MC Publishing Corp., Glen Rock, N.J., 1988 and M. and J. Ash, "Encyclopedia of Surfactants", Vol. I-III, Chemical Publishing Co., New York, 1980-1981.

Among the suitable surfactants there may be mentioned, e.g., polyacrylic acid salts, lignosulphonic acid salts, phenolsulphonic or (mono- or di-alkyl)naphthalenesulphonic acid salts, laurylsulfate salts, polycondensates of ethylene oxide with lignosulphonic acid salts, polycondensates of ethylene oxide with fatty alcohols or with fatty acids or with fatty amines, substituted phenols (in particular alkylphenols or arylphenols such as mono- and di-(polyoxyalkylene alkylphenol) phosphates, polyoxyalkylene alkylphenol carboxylates or polyoxyalkylene alkylphenol sulfates), salts of sulphosuccinic acid esters, taurine derivatives (in particular alkyltaurides), polycondensates of ethylene oxide with phosphated tristyrylphenols and polycondensates of ethylene oxide with phosphoric esters of alcohols or phenols. The presence of at least one surfactant is often required because the active substance and/or the inert vehicle are not soluble in water and the carrier agent for the application is water.

In one embodiment, commercial products will preferably be formulated as liquid concentrates whereas the end user will normally use dilute formulations.

In such liquid concentrate formulations, the concentration of the compound of active components is usually 0.001% to 70% by weight, based on the weight of the formulation, especially 1% to 40%. In one embodiment, the active components are present from 2% to 20%.

The amount of additionally added components excluding solvent, such as dispersants or surfactants, is preferably 0.1% to 40% by weight, especially 1% to 30%, or 5% to 20% each amount based on the weight of the liquid concentrate formulation.

The liquid concentrate formulations described above can be diluted to almost any ratio prior to use.

When multiple active components (fungicide:acaricide) are employed the advantageous mixing ratios of the active components are from 1:50 to 50:1, from 1:10:10:1, from 1:5 to 5:1. In one embodiment, a mixing ratio of 1:1 is preferred.

Accordingly, within these ranges, those skilled in the art will choose, on the basis of their general body of knowledge and, where appropriate, a few experiments, doses which are non-damaging to the textile substrate to be treated and suitable for use in the living environments of human beings and animals, but effective from a fungicidal and/or acaricidal standpoint. The active components typically are applied as an aqueous formulation in diluted, solubilised, emulsified or in dispersed form. Application can be made by spraying, misting, atomising, broadcasting, brushing, raking or foaming the formulation thus prepared.

In one embodiment, the active components are applied in a manner such that at least 50%, preferably at least 75%, more preferably at least 90%, by weight of the active components remaining on or in the textile substrate are present below the top surface of said textile substrate.

In one embodiment, the textile substrate is a carpet and the active components are applied in such a manner that, on average taken over the area of the treated carpet, at least 50%, preferably at least 75%, more preferably at least 90%, by weight of the active components remaining on or in the carpet are in an area comprising the bottom ½-portion of the pile to below the backing.

One particularly suitable composition contains permethrin and azoxystrobin. Another particularly suitable composition contains permethrin and fludioxonil. Yet another particularly suitable composition will contain three active components: azoxystrobin, fludioxonil and permethrin. Yet another desirable composition further contains a denaturing agent such as tannic acid or a suitable enzyme.

For example, in one embodiment, the method of the invention is carried out as follows:

(1) a suitable quantity of a liquid concentrate formulation is diluted with water to provide a dilute aqueous formulation having an active component concentration of from about 100 to about 10,000 ppm. As a specific example, a dilute solution of 2000 ppm is provided.

(2) a carpet that is susceptible to fungal infestation (and, optionally, dust mite infestation) is provided;

(3) the carpet is treated with the 100 to about 10,000 ppm dilute formulation at a rate of from 1 gallon (G)/100 sq·ft. to about 1 G/2000 sq·ft. As a specific example, a 2000 ppm solution is applied to the carpet at a rate of 1 G/800 square feet (i.e. an application rate of 100 mg a.i./m$^2$).

(4) The carpet is allowed to dry for about 0 to about 8 hours; and (5) Fungi including molds, mycelium and spores thereof, live or dead mites and faecal matter are removed from the carpet preferably by vacuuming and/or hot water extraction in a manner that does not vent such materials in to the local air. This step may be carried out prior to spraying the carpet in which case the drying step is optional (for entry by humans or animals after treatment).

Suitable application rates to a textile surface such as a carpet for the acaricide range from 10 mg to 500 mg a.i./m2; more particularly from 30 mg to 200 mg a.i./m$^2$. As a specific example, a formulation containing permethrin at 1000 ppm is applied at a rate of 1 gal/800 sq ft (100 mg a.i./m$^2$).

Textile substrates which can be treated in accordance with the method of the invention are materials comprising, for example, natural or synthetic polyamide (like wool, silk, nylon), polyurethane, polyester, polypropylene, polyethylene, polyacrylonitrile and cellulose-containing textile materials of all kinds, for example natural cellulose fibres, such as cotton, linen, jute and hemp, and also viscose staple fibre and regenerated cellulose; or blends of the above fibre materials, like polyacrylonitrile/polyester, polyamide/polyester, polyester/cotton, poly-ester/viscose and polyester/wool.

Suitable textile materials and surfaces such as carpets also include those comprising wool, synthetic polyamide, polyester, polypropylene, polyethylene, and cellulose-containing textile materials, cotton or wool. Preferred textile materials include carpets comprising synthetic polyamide fibres such as nylon 6 and nylon 6,6.

The textile material can be in different forms of presentation, as woven or knitted fabrics or as piece goods such as knitgoods, nonwoven textiles, carpets, yarn or staple fibres. Preferred are nonwoven textile materials and especially textile surfaces including carpets and wall coverings.

Numerous end use articles can be named for the treated fabrics or products made from the treated materials. Examples include but are not limited to carpets and rugs, pillow cases, bed linings, bed sheets, mattresses and mattress ticking, curtains, duvet and duvet cases, upholsteries, socks and garments.

In one embodiment, the principal active components are strobilurins or pyrroles, with azoxystrobin and/or fludioxonil being preferred, that are used alone or in combination with an acaricide such as a pyrethroid. The antifungal-properties of such active components are well known for crop protection uses and form the basis of many agricultural compositions. The invention relates to the surprising discovery that such active components are useful for controlling fungi such as molds in textile substrates that are common in many household environments.

Most importantly, however, it has been discovered that, particularly when azoxystrobin or fludioxinil are employed, the active compounds enhance the environment of the home by reducing the population of fungi such as molds (as well as dust mites when permethrin (or another suitable acaricide) also is employed) which could have a positive affect on the health of animals and human beings living in environment containing the treated textile substrate. Without wishing to be bound by any particular theory, it is believed that the active components reduce and/or inhibit fungi, molds and mites from proliferating which thereby could lead to a reduction of allergenic, toxinogenic and/or immunogenic particles that eminate from such fungi, molds and mites.

In summary, it is seen that this invention provides a method for treatment of textile materials. Variations may be made in proportions, procedures and materials without departing from the scope of the invention as defined by the following claims.

We claim:

1. A method for controlling the growth of fungi and house dust mites in a carpet comprising:
   at a rate of 10 to 500 mg a.i./m$^2$, applying an aqueous solution to the carpet,
   wherein said aqueous solution comprises a combination of active ingredients, said combination of active ingredients comprising component (a) a fungicidally effective amount of azoxystrobin, fludioxonil or a mixture thereof, and component (b) permethrin,
   wherein a ratio of component (a) to component (b) is from 1:10 to 10:1, and
   wherein said combination of active ingredients is present in a concentration of from about 100 to about 10,000 ppm of the aqueous solution.

2. The method of claim 1 wherein component (a) is azoxystrobin.

3. The method of claim 1 wherein component (a) is azoxystrobin and fludioxonil.

4. The method of claim 1 wherein the rate at which the aqueous solution is applied to the carpet is a rate of about 30 to 200 mg a.i./m$^2$.

5. The method of claim 1 wherein the rate at which the aqueous solution is applied to the carpet at is a rate of about 100 mg/m$^2$.

6. The method of claim 1, wherein the carpet comprises a pile and a backing and wherein at least 50% by weight of the combination of active ingredients remains in the carpet after said applying in an area comprising a bottom half portion of the pile to below the backing.

* * * * *